United States Patent
Retzlaff et al.

(10) Patent No.: US 10,053,664 B2
(45) Date of Patent: Aug. 21, 2018

(54) DEVICE FOR INCUBATING A SAMPLE

(71) Applicants: Ruediger Retzlaff, Birkenfeld (DE);
Alexander Falkner, Birkenfeld (DE)

(72) Inventors: Ruediger Retzlaff, Birkenfeld (DE);
Alexander Falkner, Birkenfeld (DE)

(73) Assignee: STRATEC Biomedical AG, Birkenfeld (DE)

(*) Notice: Subject to any disclaimer, the term of this patent is extended or adjusted under 35 U.S.C. 154(b) by 508 days.

(21) Appl. No.: 13/905,697

(22) Filed: May 30, 2013

(65) Prior Publication Data
US 2013/0323775 A1 Dec. 5, 2013

(51) Int. Cl.
*B01L 7/00* (2006.01)
*C12M 1/00* (2006.01)
*B01F 11/00* (2006.01)

(52) U.S. Cl.
CPC .......... *C12M 41/14* (2013.01); *B01F 11/0042* (2013.01); *B01L 7/00* (2013.01); *B01L 2300/0809* (2013.01); *B01L 2300/1816* (2013.01)

(58) Field of Classification Search
CPC .................. C12M 41/14; B01L 7/00
USPC ....................................... 436/174
See application file for complete search history.

(56) References Cited

U.S. PATENT DOCUMENTS

| 3,539,156 A * | 11/1970 | Zipperer ............ B01F 11/0034 366/110 |
| 3,781,503 A * | 12/1973 | Harnden, Jr. ....... A47J 36/2483 219/622 |
| 3,989,916 A * | 11/1976 | Amagami ............ H02M 7/523 219/622 |
| 5,412,171 A * | 5/1995 | Yahav .................... A47J 27/14 219/621 |
| 5,593,228 A | 1/1997 | Tannenbaum |
| 5,968,398 A * | 10/1999 | Schmitt ................. H05B 6/062 219/620 |
| 2005/0158725 A1* | 7/2005 | Yukimasa ............. C07H 21/00 435/6.12 |
| 2012/0306824 A1* | 12/2012 | Horie .................. G06F 3/03545 345/179 |

FOREIGN PATENT DOCUMENTS

| CN | 201676659 | 12/2010 |
| CN | 201815320 | 5/2011 |
| GB | 1215604 | * 12/1970 |
| JP | 58112055 | 7/1983 |
| WO | 2011/141132 | 11/2011 |

* cited by examiner

*Primary Examiner* — Christopher Adam Hixson
*Assistant Examiner* — Emily R. Berkeley
(74) *Attorney, Agent, or Firm* — 24IP Law Group; Timothy R. DeWitt

(57) ABSTRACT

The field of the invention relates to a device for incubating a sample. The present disclosure provides an incubator for shaking and/or heating at least one sample. The device comprises at least one inductor placed below an induction heating plate. A heat conducting plate is mounted onto the induction heating plate. The device further comprises a moving arrangement for placing the sample onto the heat conducting plate.

12 Claims, 5 Drawing Sheets

DEVICE FOR INCUBATING A SAMPLE

CROSS-REFERENCE TO RELATED APPLICATION

This application claims benefit of and priority to UK Patent Application No. GB 9209708.5 filed on 31 May 2012 by the same inventors.

FIELD OF THE INVENTION

The field of the invention relates to a device and a method for incubating a sample.

BACKGROUND OF THE INVENTION

Automated analyser systems for use in clinical diagnostics and life sciences are produced by a number of companies. For example, the Stratec Biomedical AG, Birkenfeld, Germany, produces a number of devices for specimen handling and detection for use in automated analyser systems and other laboratory instrumentation.

Existing incubators used in laboratories use heating foils or hot air for heating a sample. Heating foils need a supply of electrical energy through cables in order to produce heat. Air, often used as an insulator, has a low heat capacity and a low thermal conductivity making the process of heating of the sample slower.

Existing incubation methods often comprise shaking the sample. When using heating foils care has to be taken that the cables supplying the heating foils with electrical energy do not suffer. Using flexible cables allows for shaking of the sample.

International patent application No. WO 2011/141132 A1 discloses an apparatus for mixing and controlling the temperature of laboratory vessel contents. The apparatus comprises a drive for moving a lower accommodating device in order to mix the laboratory vessel contents placed on an upper exchangeable block. The apparatus further comprises a temperature control device with a heat source or sink. The temperature control device is in a heat conducting connection with the exchangeable block. The energy supply connection to the temperature control device or the heat conduction connection has to be flexible to permit the moving of the exchangeable block.

The U.S. Pat. No. 5,593,228 discloses a rotary shaker for driving laboratory flasks to move along orbital paths in order to mix materials contained in the laboratory flasks. The laboratory flask or the materials contained are not heated. The teachings of this prior art disclosure do not permit incubation of cultures or samples at varying predetermined temperatures.

Chinese utility model No. CN 201676659 U discloses a thermostatic mixing instrument with an eccentric oscillation drive means driving a transmission frame and a radiator for heating a cooling and heating body on the transmission frame. An energy supply to the radiator has to be flexible to permit moving of the transmission frame.

Induction heating is used in devices such as induction cookers or induction furnaces for conducting heat produced to an object to be heated. Induction heating is used in areas such as the treatment of surfaces or when melting, brazing, soldering or welding metals. Induction heating used in incubators is not known in the art.

Japanese patent application No. JP 58112055A discloses a magnetically heated container comprising a heat generating magnetic body in which heat is produced by a high frequency inductor. The magnetically heated container is not adapted to be moved with respect to the inductor or to be shaken. Thus, the magnetically heated container does not provide mixing of samples therein.

U.S. published patent application No. U.S. 2005/0158725 A1 discloses a reaction container comprising a heat generating portion. Heat is produced in the heat generating portion by induction using a heating coil. The reaction container is not adapted to be moved with respect to the heating coil or to be shaken. Thus, the magnetically heated container does not provide mixing of samples therein.

Chinese utility model No. CN 201815320 U discloses a metal plate covered by asbestos layers for emitting heat into an electromagnetic oven. The electromagnetically heated metal plate, heats a beaker or glass container filled with a solution. The beaker or the glass container are not adapted to be moved with respect to the metal plate or to be shaken. Thus, samples placed in the beaker or the glass are not mixed.

In induction heating, heat is produced in a magnetic body from energy transported to the magnetic body through an electromagnetic field, i.e. without using cables or other conducting means. The energy transported through an electromagnetic field produced by induction can also be used to supply energy to moving bodies.

SUMMARY OF THE INVENTION

The present disclosure provides a device for incubating a sample. Incubating within the meaning of the present disclosure shall mean heating and/or shaking. The incubator comprises at least one inductor placed below an induction heating plate. A heat conducting plate is mounted onto the induction heating plate. The incubator further comprises a means for moving at least the at least one sample placed onto the heat conducting plate.

The means for moving at least the at least one sample may move the induction heating plate, the heat conducting plate and the sample placed on the heat conducting plate.

The induction heating plate may comprise a ferromagnetic material.

The induction heating plate may comprise steel.

The heat conducting plate may comprise aluminium.

The incubator may further comprise a capacitor switched parallel to the inductor.

The incubator may further comprise a metal-oxide-semiconductor field-effect transistor driver connected to a circuit comprising the inductor and the capacitor.

The incubator may further comprise a microcontroller connected to the metal-oxide-semiconductor field-effect transistor driver.

A method for incubating the at least one sample is disclosed. The method comprises generating an alternating current in the inductor and thereby producing heat in the induction heating plate. The method further comprises conducting the heat to the at least one sample through the heat conducting plate. The method further comprises moving at least the least one sample.

The generating of the alternating current in the inductor may further comprise driving the circuit comprising the inductor and the capacitor to oscillate resonantly.

The generating of the alternating current in the inductor may further comprise generating a square wave signal by a microcontroller and transforming the square wave signal for driving the circuit comprising the inductor and the capacitor.

The use of an incubator as disclosed above is intended for heating and/or shaking of at least one sample, wherein the incubator may be used as part of a diagnostic or analytic system.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

While various embodiments of the present invention have been described above, it should be understood that they have been presented by way of example, and not limitation. It will be apparent to persons skilled in the relevant arts that various changes in form and detail can be made therein without departing from the scope of the invention.

The various embodiments and aspects of the present disclosure are used, for example, in analyser systems and other laboratory instruments in the fields of clinical diagnostics, forensic science and life sciences.

The present disclosure relates to a device and a method using induction heating in automated analyser systems, e.g. for diagnostic purposes. More particularly, the disclosure relates to an incubator using induction heating for the heating of at least one sample.

The incubation of the at least one sample is accelerated by the induction heating. In particular, if the incubation of the at least one sample takes place at a predetermined optimal temperature, the incubation of the at least one sample is accelerated.

The present disclosure allows for a separation of energy supply and heat production. More particularly, the present disclosure allows for a separation of an energy supply and an induction heating object producing the heat and conducting the heat to the at least one sample.

In the present disclosure an energy supply feeds an alternating current to an inductor producing an electromagnetic field. The electromagnetic field spreads through space and produces heat in an induction heating plate conducting the heat through a heat conducting plate to the at least one sample.

The separation of the energy supply and the inductor from the induction heating plate carrying the at least one sample allows for a shaking of the at least one sample together with the induction heating plate and heat conducting plate without having to take care for an energy supply through, for example, a cable.

The energy supply for heat production and the place of heat production are spatially separated from each other. Thereby, no flexible energy supply connection to the place where heat is produced is required for permitting the shaking of the at least one sample.

Figure 1:
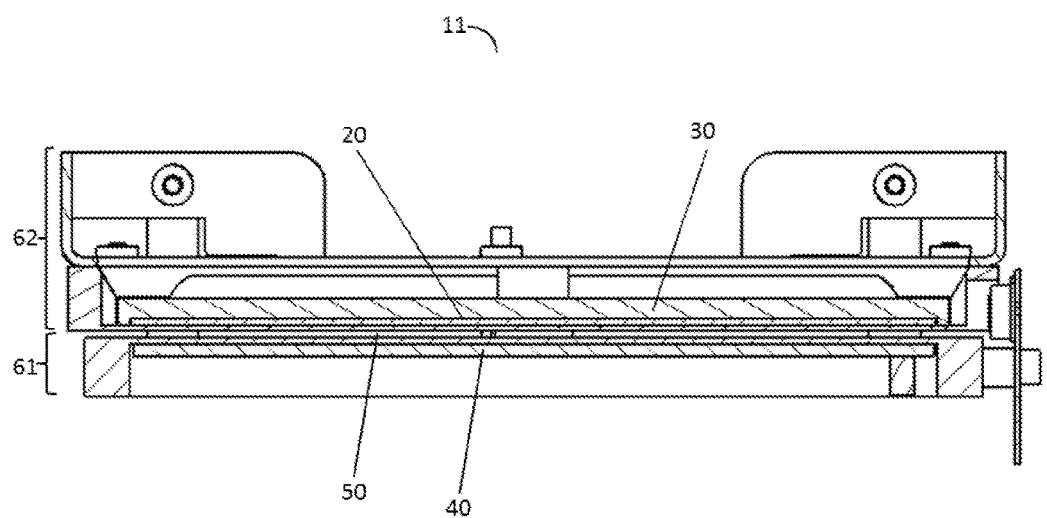
FIG. 1 shows a cross-sectional view of an incubator according to the disclosure.

FIG. 1 shows a sectional view of an inner part 11 of an incubator 10 (see FIGS. 4 and 5) according to the disclosure. The incubator 10 comprises an induction heating plate 20 and a heat conducting plate 30. At least one sample is placed onto the heat conducting plate 20 during incubation of the at least one sample.

The induction heating plate 20 comprises a ferromagnetic material. In one aspect of the disclosure the induction heating plate 20 comprises steel.

The incubator 10 further comprises an inductor 40, placed below the induction heating plate 20. The inductor is connected to an energy supply feeding an alternating current to the inductor 40. The alternating current flowing through the inductor 40 generates an electromagnetic field that spreads through space. The electromagnetic field produces heat in the induction heating plate 20.

The heat produced in the induction heating plate 20 is conducted via the heat conduction plate 30 to the at least one sample.

The inductor 40 is placed in a lower part 61 separated from an upper part 62 comprising the induction heating plate 20, the heat conduction plate 30 and the at least one sample by an air gap 50. The air gap 50 leaves room for the upper part 62 to be moved for shaking the at least one sample.

The at least one sample can be shaken. This provides mixing of the at least one sample and thus accelerates incubation of the at least one sample.

Figure 2:
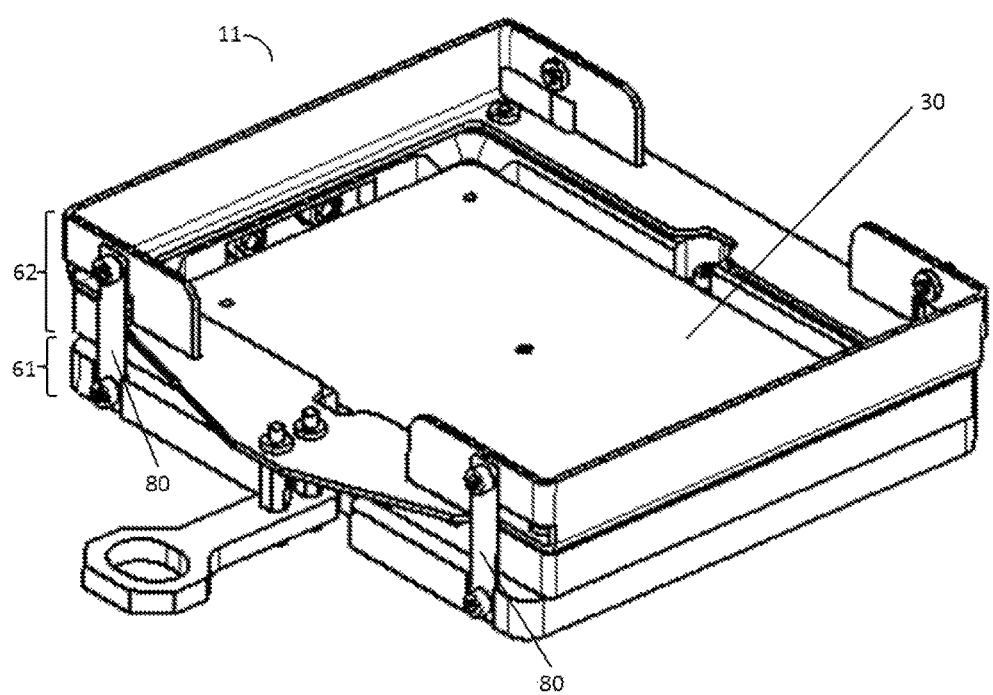
FIG. 2 shows a perspective view of an incubator according to the disclosure with arms suitable for moving the upper part of the incubator.

FIG. 2 shows an aspect of the disclosure with a plurality of arms 80 flexibly connected to the lower part 61 and the upper part 62. The plurality of arms 80 may be actuated such that the upper part 62 carrying the at least one sample 10 moves relative to the lower part 62.

Because the energy for producing the heat in the induction heating plate 20 is transported by the electromagnetic field, no energy supply, for example through a cable, to the upper part 62 is necessary. As a result no care needs to be taken that an energy supply for heat production does not suffer from the moving of the upper part 62.

Figure 3:
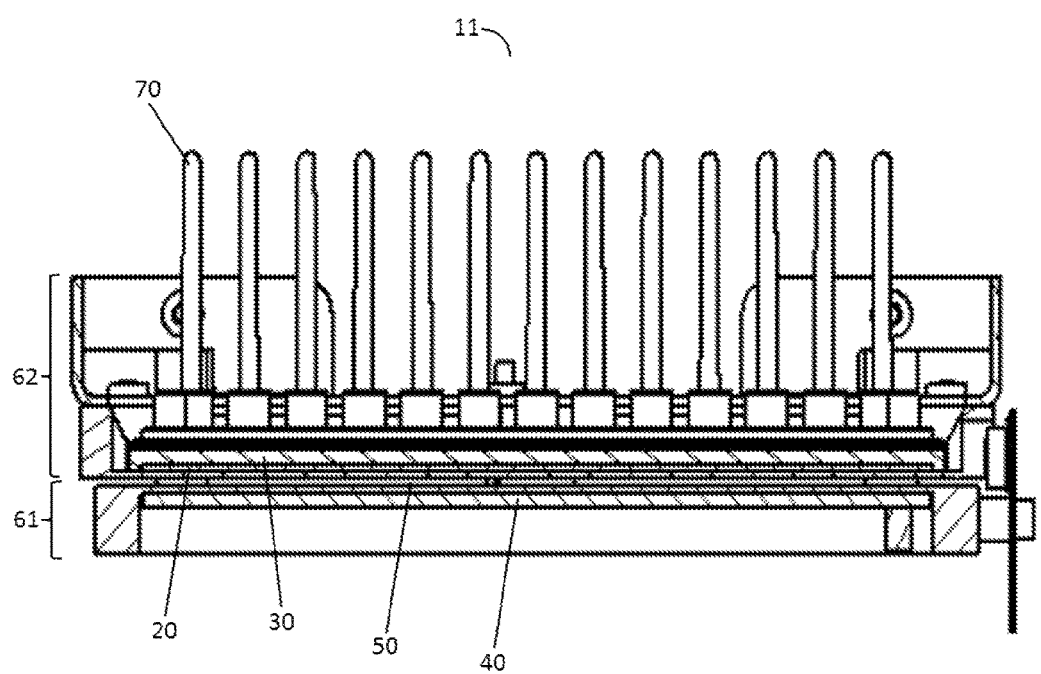
FIG. 3 shows an aspect of the disclosure with a sample carrier placed onto the heat conducting plate.

In an aspect of the disclosure a sample carrier called "hedgehog" 70 (see FIGS. 3 and 4) is placed onto the heat conducting plate 30. The hedgehog is a rack for placing deep-well at least one microplate therein. The at least one sample is placed into the at least one microplate.

Figure 4:
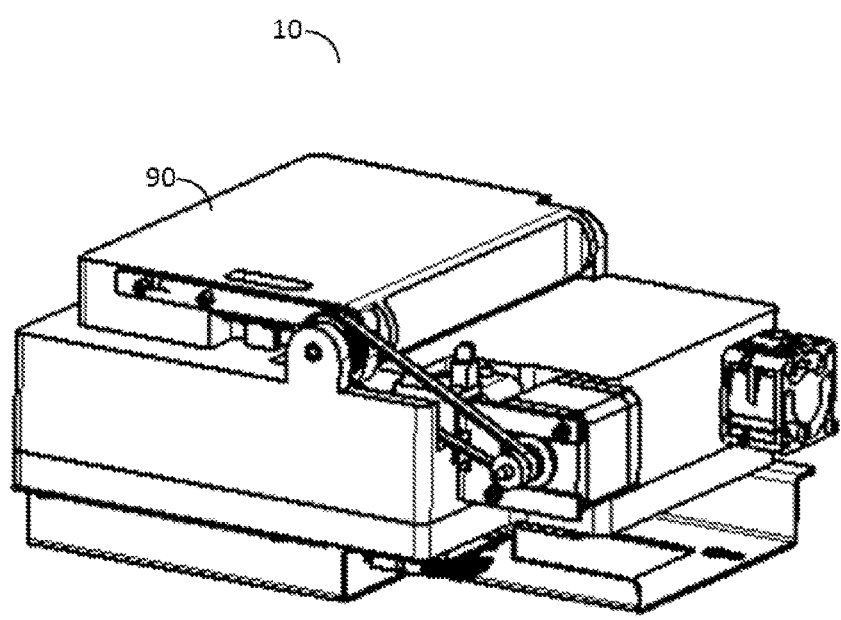
FIG. 4 shows a perspective view of an incubator having a cover according to the disclosure.
Figure 5:
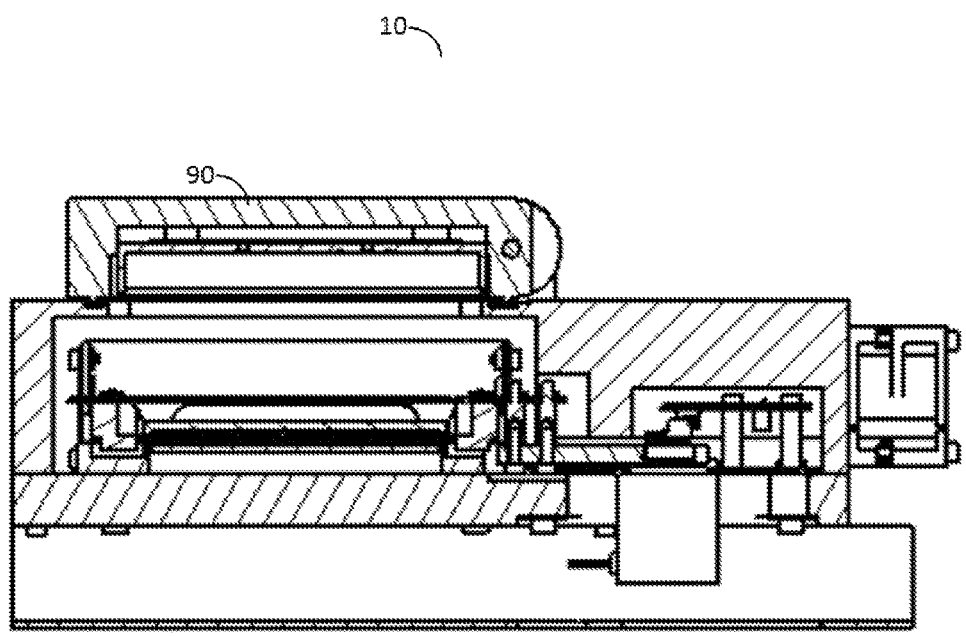
FIG. 5 shows a cross-sectional view of an incubator having a cover according to the disclosure.

In a further aspect of the disclosure the incubator 10 comprises a cover 90 (see FIGS. 4 and 5). It is conceivable that the cover 90 is heated. Heating of the cover 90 prevents water of condensing on the cover. Furthermore the air surrounding the at least one sample warms up when the cover 90 is closed resulting in a faster heating of the at least one sample and less loss of energy

LIST OF REFERENCE NUMBERS

10 Pump
11 Inner part
20 Heating plate
30 Heat conducting plate
40 Inductor
50 Air gap 61 Lower part
62 Upper part
70 Sample carrier "hedgehog"
80 Arms
90 Cover

The invention claimed is:

1. A device for incubating at least one sample, comprising at least one lower part with an inductor placed spatially separated below an upper part with an induction heating plate with a heat conducting plate mounted thereon for placing the at least one sample onto the heat conducting plate, wherein the lower part and the upper part are separated by an air gap with a plurality of arms flexibly connected to the lower part and the upper part, wherein the plurality of arms can be actuated for shaking of the at least one sample together with the induction heating plate and the heat conducting plate.

2. The device according to claim 1, wherein the induction heating plate comprises a ferromagnetic material.

3. The device according to claim 1, wherein the induction heating plate comprises steel.

4. The device according to claim 1, wherein the heat conducting plate comprises aluminum.

5. The device according to claim 1, further comprising a capacitor switched parallel to the inductor.

6. The device according to claim 5, further comprising a metal-oxide-semiconductor field-effect transistor driver connected to the circuit comprising the inductor and the capacitor.

7. The device according to claim 6, further comprising a microcontroller connected to the metal-oxide-semiconductor field-effect transistor.

8. A method for incubating at least one sample comprising
generating an alternating current in a lower part of a the device of claim 1 comprising the inductor and thereby producing heat in the spatially separated upper part of the device comprising the induction heating plate,
conducting the heat to at least one sample through the heat conducting plate mounted onto the induction heating plate, and
moving at least the at least one sample by actuating the flexibly to the lower part connected upper part.

9. The method according to claim 8, wherein the generating of an alternating current in the inductor comprises driving the circuit comprising the inductor and the capacitor to oscillate resonantly.

10. The method according to claim 8, wherein the generating of the alternating current comprises generating a square wave signal by a microcontroller and transforming the square wave signal for driving the circuit comprising the inductor and the capacitor.

11. The method according to claim 8, further comprising at least one of heating or shaking of the at least one sample.

12. An analyser system for analysing a sample comprising:
an incubator comprising at least one lower part with an inductor placed spatially separated below an upper part with an induction heating plate with a heat conducting plate mounted thereon for placing the at least one sample onto the heat conducting plate,
an induction heating plate having a heat conducting plate mounted thereon; and
a moving arrangement for placing the sample onto the conducting plate, wherein
the lower part and the upper part are separated by a gap and flexibly connected with each other by a plurality of arms, wherein the plurality of arms can be actuated for shaking of the at least one sample placed onto the heat conducting plate together with the induction heating plate and heat conduction plate.

* * * * *